US010981950B2

(12) United States Patent
Pezzini (10) Patent No.: US 10,981,950 B2
(45) Date of Patent: Apr. 20, 2021

(54) THERAPEUTIC PROTEIN FLOW KIT FOR A CONTINUOUS PURIFICATION SYSTEM (71) Applicant: Joanna Pezzini, Burke, VA (US)

(72) Inventor: Joanna Pezzini, Burke, VA (US)

(*) Notice: Subject to any disclaimer, the term of this patent is extended or adjusted under 35 U.S.C. 154(b) by 230 days.

(21) Appl. No.: 16/263,855

(22) Filed: Jan. 31, 2019

(65) Prior Publication Data

US 2020/0247844 A1 Aug. 6, 2020

(51) Int. Cl.
*B01D 15/18* (2006.01)
*B01L 3/00* (2006.01)
*B01D 15/08* (2006.01)
*C07K 1/36* (2006.01)
*C07K 1/22* (2006.01)

(52) U.S. Cl.
CPC ............ *C07K 1/36* (2013.01); *B01D 15/1871* (2013.01); *C07K 1/22* (2013.01)

(58) Field of Classification Search
CPC ........ C07K 1/36; C07K 1/22; B01D 15/1871; B01D 15/08; B01L 3/502; G01N 33/53
See application file for complete search history.

(56) References Cited

U.S. PATENT DOCUMENTS

| 4,693,834 | A | 9/1987 | Hossom |
| 8,012,584 | B2* | 9/2011 | Sugiura ............ F17C 1/06 428/408 |
| 8,920,645 | B2 | 12/2014 | Moran et al. |
| 2002/0110495 | A1 | 8/2002 | Hunt et al. |
| 2015/0133636 | A1* | 5/2015 | Xenopoulos ............ C07K 1/36 530/387.1 |

FOREIGN PATENT DOCUMENTS

WO   WO2018/210644   * 11/2018   ............. B01D 61/18

OTHER PUBLICATIONS

Rucker-Pezzini J, Arnold L, Hill-Byrne K, Sharp T, Avazhanskiy M, Forespring, C. Single pass diafiltration integrated into a fully continuous mAb purification process. *Biotechnology and Bioengineering.* 2018;1-9.
Arnold, Lee, Rucker-Pezzini and Lee, Implementation of Fully Integrated Continuous Antibody Processing: Effects on Productivity and COGm, Biotechnology Journal, 2018; 1-10.

* cited by examiner

Primary Examiner — Jennifer Wecker
Assistant Examiner — Jonathan Bortoli
(74) Attorney, Agent, or Firm — William Gray Mitchell (57) ABSTRACT A compact flow kit for the continuous purification of serums containing therapeutic proteins, manufactured to minimize the risk of leakage or contamination from flexible tubing attachments.

11 Claims, 5 Drawing Sheets

THERAPEUTIC PROTEIN FLOW KIT FOR A CONTINUOUS PURIFICATION SYSTEM

CROSS REFERENCE TO RELATED APPLICATIONS

Not applicable

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The present invention relates to a therapeutic protein flow kit for a continuous purification system.

Background of the Invention

Single-use devices for the purification of therapeutic drugs and other fluid substances are known in the market. Such devices have historically involved flexible (e.g. rubber or plastic) tubing connecting various required containers, instrumentation and purification devices (i.e. filters and chromatography columns). Each time that a flexible or replaceable tube or line is used to transmit fluids from one containment vessel to another, there exists the possibility of leakage and/or contamination of the fluid at each connection point. As such, it is preferable to replace as many connections and as much tubing as possible with hard, integrated components to provide for permanent, leak- and contamination-proof flow of the subject fluids.

In particular, the use of therapeutic fluid serums containing antibodies, interferon or other therapeutic proteins are essential for the treatment of myriad autoimmune and inflammatory diseases. The disorders associated with such treatment are many and often well-known, including crohn's disease, colitis, lupus, multiple sclerosis, psoriasis and others. The mechanisms by which therapeutic proteins treat the manifestations of such disorders are varied and, to ensure an effective response in specifically targeted tissue, it is essential that a given serum be properly formulated to contain the appropriate target protein(s) in the appropriate concentration(s), without the presence of extraneous proteins or other types of contamination.

Methods for continuous manufacture of antibodies and other therapeutic proteins have been developed due to their improved efficiency, flexibility, and productivity over traditional batch processes. These methods do not hold the entirety of the batch product in a single tank, but merely hold sufficient product to ensure a homogeneous solution of the therapeutic protein or antibody at the inlet to a given purification step. A common monoclonal antibody purification process will consist of a Protein A affinity chromatography step, a low pH viral inactivation step, an anion exchange step (membrane or chromatography), a virus filtration step, a cation exchange chromatography step, and a diafiltration and concentration step. These steps typically provide orthogonal means of removing impurities that include DNA, viruses, host cell proteins, product impurities, etc. A traditional batch process would hold a 200 L batch in a 200 L tank between each of the described steps, in comparison to a 200 mL to 2 L vessel used in a continuous process. Reduced flow rates of the process allow for reduced piping or tubing sizes from ½" to ⅛", for the same size batch. This reduction in equipment size provides new opportunities for flow kits that directly meet the needs of a continuous process.

Flow kits are known devices for the mixing of components of therapeutic serums, including those containing antibodies. A flow kit for production of a therapeutic protein serum will contain one or more vessels for mixing, with one or more inflow pathways for the addition of components, one or more pathways to allow for testing of contents and one or more pathways for extraction of the product. The presence of each such pathway necessarily carries the risk of leakage of a percentage of valuable product, as well as the risk of ingress of one or more contaminating substances, such as dust, bacteria, viruses or chemicals. The presence of such contaminants in a therapeutic serum introduced into a patient may produce results ranging from the inefficacy of the serum to the introduction of harmful substances into the patient's body.

Additionally, known flow kits and purification systems comprising such kits tend to require large amounts of lab space. This is due to the reliance of such kits on many individual components connected with lines or tubing, which necessarily requires space to lay out and connect the components. The use of a single, integral flow kit design can substantially decrease the space needed and thus lower lab space expenses. Further, a lack of multiple components to be assembled and attached significantly lowers the manufacturing cost and complexity of each kit, while the likelihood that cracks or leaks will form over time in a single integrated design is much lower and thus increases durability.

Such known designs appear in U.S. Pat. No. 4,693,834 to Hossom. and U.S. Pub. 2002/0110495 to Hunt et al. Hossom shows multiple chambers created by the assembly of various components that are attached by pinning and screws, while Hunt shows a plethora of free-standing chambers with connection lines and tubing leading from one chamber to the next.

What is needed is an integral flow kit device, manufactured with 3D printing, injection molding or similar technology to minimize the number of flexible connectors required, thus minimizing the potential for leakage and contamination, increase kit durability and decrease lab space requirements. The invention describes herein provides such advantages.

BRIEF DESCRIPTION OF THE INVENTION

In a preferred embodiment, a flow kit for the continuous purification of a therapeutic protein serum product, made of plastic, forming a single, compact, integrated piece comprising a static mixer, a mixing vessel, a plethora of input and outlet lines for the products and the addition of adjusting or processing solutions, a pH probe connection and a sampling connection.

In another preferred embodiment, the flow kit as described herein, wherein the manufacturing process is taken from the group consisting of 3D printing, injection molding, low-pressure molding such as gas-assist molding or structural-foam molding, coinjection, in-mold polymerization, blow molding, shaped thermoforming or another similar method.

In another preferred embodiment, the flow kit as described herein, wherein the plastic is HP 3D High Reusability PA 12 or another commercially available plastic with similar characteristics.

In another preferred embodiment, the flow kit as described herein, wherein the flow kit is made of carbon fiber.

In another preferred embodiment, the flow kit as described herein, wherein the kit is connected by flexible tubing to a separate purification device such as a filter or chromatography column.

In another preferred embodiment, the flow kit as described herein, wherein the kit is disposable.

In another preferred embodiment, the flow kit as described herein, wherein the kit is detachable, cleanable and reusable.

In another preferred embodiment, the flow kit as described herein, wherein the kit processes the therapeutic protein serum by optionally mixing with an adjustment solution(s) in the static mixer, delivering the serum to a separate purification device, then optionally mixing the serum with adjustment solution(s) in the mixing vessel.

In another preferred embodiment, a therapeutic protein serum continuous purification system comprising one or more powered pumps, multiple solution containers, multiple flow kits of claim 1, such flow kits interspersed with multiple filters and/or chromatography columns and a collection vessel, each connected by flexible tubing.

In another preferred embodiment, a method of purifying a therapeutic protein serum comprising the steps of:
Connecting a supply of unpurified protein serum to a first flow kit of claim 1, and into a static mixer of the kit,
Connecting a supply of a first adjustment solution(s) to the static mixer,
Mixing the first adjustment solution(s) and serum in a static mixer,
Directing the serum from the static mixer into a separate filter or chromatography column for processing,
Directing the serum from the separate filter or chromatography column into the flow kit and into a mixing vessel,
Connecting a supply of second adjustment solution(s) to the mixing vessel,
Mixing the first adjustment solution(s) and serum in a mixing vessel, and
Directing the serum from the mixing vessel out of the kit and to another separate flow kit or a collection vessel.

DETAILED DESCRIPTION OF THE INVENTION

The invention is a flow kit to be employed in the continuous purification of therapeutic protein serum. A major point of novelty of the invention is the use of a single, integrated device comprising both a static mixer and mixing vessel, along with multiple lines and ports for the introduction of adjusting and processing solutions, as well as for ingress and egress of the product before, during and after processing. The integral nature of the kit provides for a compact device that can be seated alone or in a bank of multiple kits, minimizing flow path links and thus utilizing far less lab bench space than with previous non-integral versions. The compact design is enabled by vertical orientation of a static mixer and necessary probes, and the probes' direct attachment to the mixer via 3D printing of necessary ports. This enables the entire flow path to rest on top of a scale and stir plate in the lab.

Kits may be at least as small as 6.25 cm length, 4 cm width and 7.25 cm height, or as much as 10 times such size. In one preferred embodiment, the flow kit dimensions are approximately 12.5 cm length×8 cm width×15.5 cm height. A flow kit of such size can process 50 L cell culture (with 5 g/l titer) per day. The mixing vessel should be sized such that, at the flow rates used, the residence time provides sufficient mixing to achieve a homogenous solution. Flow rates are determined by pressure limitations for a given tube diameter. Larger and smaller tubes and vessel sizes within the kit and without it may be used to increase or decrease the flow rate and to fit the space available for setup.

Ideal vessel volume sizes for the described flow kit may run from 0.2 ml to 200 L. In preferable range, such kit would accommodate from 250 ml to 5 L of fluid. In a more preferred range, the kit would accommodate 500 ml to 2 L.

Further, 3D printing enables multiple kits to form a system with little or no installation or support infrastructure to ensure correct orientation of components. The described kits can instead be laid out on a tabletop or rack in rows without further need for stabilization. Such a system would comprise a power source, one or more powered pumps to move serum through the system, multiple flow kits and one or more filters or chromatography columns attached to each kit, with the last kit in the system flowing into a collection vessel. A purification system involving multiple integral kit units would allow for each unit to be discretely removed and replaced with only a few seconds' disruption to the system's processing. Thus, the units themselves operate disposably should any given unit become clogged or otherwise nonfunctional.

The manufacturing process of the integral device is to be taken from the group comprising, without limitation, 3D printing, injection molding, low-pressure molding such as gas-assist molding or structural-foam molding, coinjection, in-mold polymerization, blow molding, shaped thermoforming or another similar commercially known method.

The material used for the flow kit must provide rigidity to allow for durability and the attachment of flexible tubing and/or the connection of other devices such as filters or probes, as well as acceptably low in toxicity. In a preferred embodiment, the flow kit is made of USP Class VI plastic, which has been tested as safe for pharmaceutical processing use with an acceptable toxicity profile, for example, HP 3D High Reusability PA 12. Such plastic also provides excellent chemical resistance which enables chemical sanitization with acid and base solutions. Such material also has thermal properties allowing for sanitization with steam.

In an alternate embodiment, the kit is made of another known plastic exhibiting sufficient rigidity and durability and usable in one of the preferred methods of manufacture. Available plastics especially useful in 3D printing include acrylonitrile butadiene styrene (ABS), polyactic acid (PLA), polyvinyl chloride (PVC), polyethylene terephthalate (PET), PET with T-glase (PETT), copolyesters such as PETG, and polystyrene or high-impact polystyrene (HIPS). Carbon fiber would also be a preferred material. In an alternate embodiment, the material could be a commercially appropriate metal or alloy such as aluminum or stainless steel.

The fluid flow through the kit itself and through any system comprised of multiple kits will be initiated and maintained by one or more powered, external pumps. In a given continuous purification system, a powered pump will generate pressure to push untreated serum into the initial flow kit, and additional pumps may be located between kits or between a kit and filter or chromatography column as needed.

The main components of the integral flow kit are a static mixer and instrument ports on one side and vented mixing vessel on the other, each embodied as a chamber within the kit body accessed by various channels (also referred to as lines) also within the kit body. As therapeutic protein serum product is introduced to the kit through an external input line, such line transmits the product directly into the static mixer space. A separate input line for adjusting or processing solutions, such as acid, base or buffer, also flows directly to the static mixer, wherein such solution(s) is mixed with the newly introduced serum product to achieve the desired pH, conductivity, or buffer concentration. Said mixture is then transported through a static mixer, through instrument and sample ports and to a port with a hose barb for transportation out of the kit and towards a separate purification device comprising either a filtration device or a chromatography column.

Instruments connected to the instrument ports ensure the serum has the appropriate physical (pressure) and chemical (pH and/or conductivity) properties to safely load onto the chromatography column or filter and achieve the intended impurity removal, respectively. The purification technologies (i.e. chromatography column or filtration device) provide orthogonal means of purification of the therapeutic protein serum, commonly based on product or impurity charge profiles (cation or anion exchange resins and filters), molecular size (virus filtration, microfiltration, or size exclusion chromatography), or hydrophobicity (chromatography resins or filters). These technologies are staged consecutively to purify, concentrate and change the buffer composition of the protein (i.e. diafiltration). A single flow kit can be used with a single chromatography column or filtration device or multiple columns or filters may be connected in series or parallel within a single flow kit (ex. a depth filter, 0.2 um filter to minimize bioburden, anion exchange filter and virus filter can all be connected in series without exceeding pressure limitations).

Upon completion of the purification step, the therapeutic protein serum is redirected to the flow kit via flexible tubing connected to a mixing vessel input line, thereby flowing directly into the mixing vessel. A separate mixing vessel solution input line, designed to be sub-surface, is also located on the outer surface of the kit and can be attached to flexible tubing providing for input of further adjusting or processing solutions such as, but not limited to, acid or base. For example, this line can be used to neutralize the pH of the product or adjust the pH, conductivity or concentration of the product to meet the requirements of the subsequent step. Alternatively, this line can be used to siphon diafiltration buffer to provide continuous diafiltration in combination with inline concentration membranes. The mixing vessel also comprises a vent or filter attachment embodied as another line between the mixing vessel and the outer surface of the kit body, such vent to create a pressure break for a reduction or elimination of pressure within the mixing vessel. Upon the mixing of serum and solution(s) in the mixing vessel, the resulting processed therapeutic protein serum product is then directed out of the flow kit via a product outlet line and toward another kit for further processing, or a separate collection vessel.

In a standard embodiment, the static mixer is used to adjust the serum to meet the pH, conductivity and concentration profile required to perform purification on the chromatography or filtration device. Then, the mixing vessel is used to adjust the pH, conductivity or concentration of the product after it leaves the purification device to ensure it is stable or to achieve the desired composition for the subsequent step or final product collection.

Examples of such adjustment include, without limitation,
1. Low pH viral inactivation requires inline adjustment with acid to pH of approximately 3.5 through the static mixer line before the product enters the chromatography column and then requires neutralization in the mixing vessel (after the serum leaves the column) to prevent product degradation. Note: the column provides the required residence time at a low pH to provide viral inactivation.
2. Single-pass diafiltration requires no inline adjustment with the static mixer prior to use of the tangential flow filtration (TFF) membrane but requires addition of diafiltration buffer into the mixing vessel to dilute the product to its original (or newly specified) concentration. Diafiltration is achieved with multiple (at least three) flow kits in series, each attached to one TFF membrane, to provide consecutive concentration and dilution steps.

Connection components of the flow kit, such as connections for pH probes or sampling, are to be embodied as tri-clamp ports. Such ports may be fitted with rubber or rubber-like gaskets to effect a leak-proof seal. Similarly, the ends of various input and outlet lines extending outward from the kit body each end in a flared port barb to allow for a tight overlay of flexible tubing for the fluid moving towards or away from the kit. Such port barbs may be integral to the kit and overlayed with a layer of rubber or rubber-like plastic to create a tight seal with the flexible tubing, luer locks or similar known fluid transmission features. Alternatively, the barbs themselves may be made of such rubber-like material. All such gaskets, o-rings, barbs or barb covers may be removable and replaceable with wear.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

DETAILED DESCRIPTION OF THE FIGURES

Figure 1:
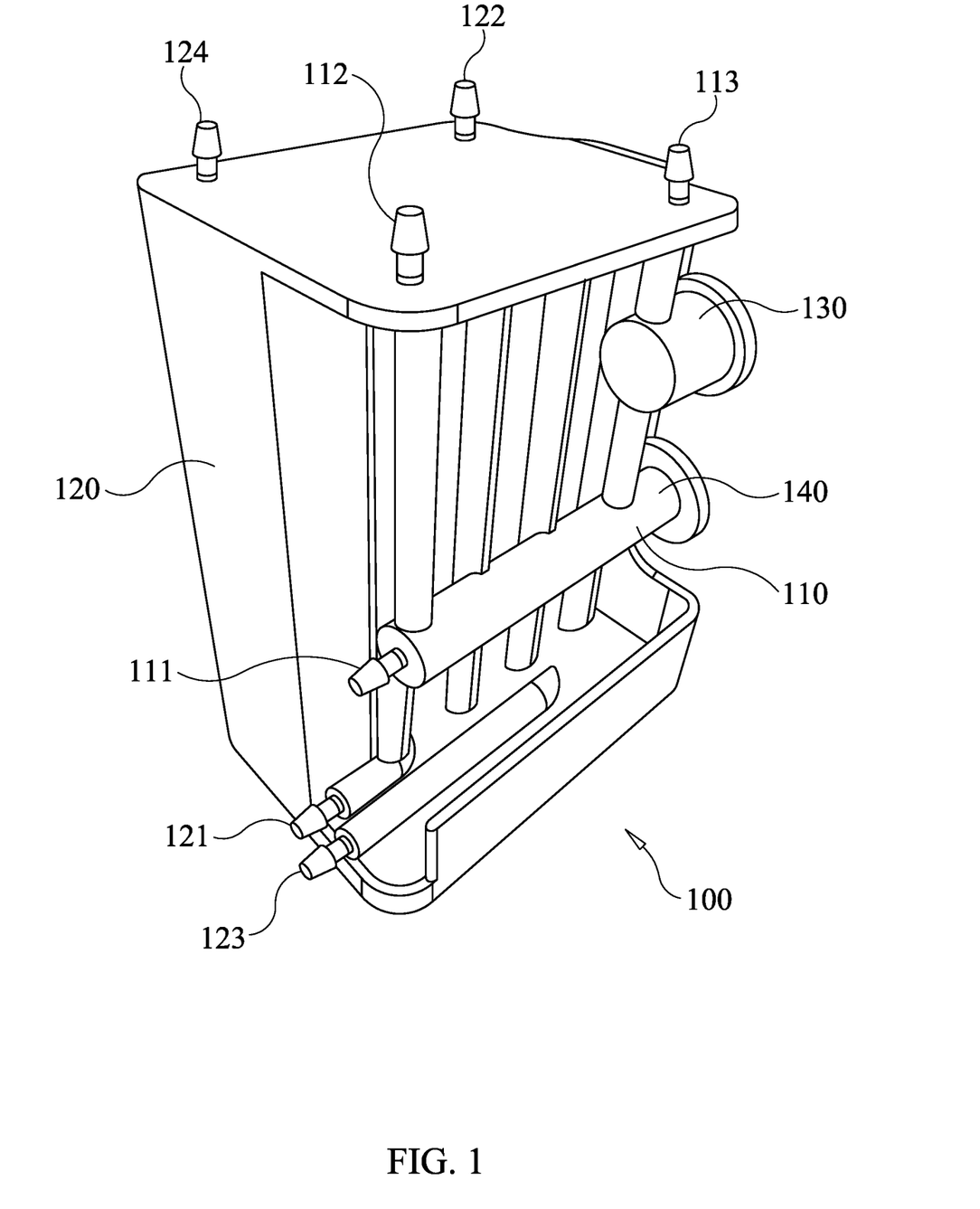
FIG. 1 is a line drawing evidencing a perspective view from the static mixer side of a flow kit for the purification of therapeutic protein serum.

FIG. 1 shows a perspective view of a flow kit 100 for the purification of therapeutic protein serum as seen from the from the static mixer 110 side. The therapeutic protein serum to be processed by the flow kit 100 is introduced through product input line 112 and flows directly into static mixer 110. As required, adjusting or processing solutions can be added to static mixer solution input line 111, which also flows directly into static mixer 110. An external pump (not pictured) pushes the mixture of serum and solutions through a static mixer, through a sampling connection 140 and a pH probe connection 130, and finally out through a second end of such outlet line 113, such second end also comprising a port barb to which another flexible tube (not pictured) can be attached, thereby directing the processed therapeutic protein serum to a separate purification technology device (not pictured), which will either consist of a filtration device or chromatography column.

The pH probe connection 130 is embodied as an open port into which a pH measuring device may be inserted and/or locked, to measure the pH level of the therapeutic protein serum after processing in the static mixer 110. The sampling connection 140 is embodied similarly as an open port into which a sampling device (not pictured) may be inserted and/or locked to collect a sample of the therapeutic protein serum after processing in the static mixer for further testing.

Figure 2:
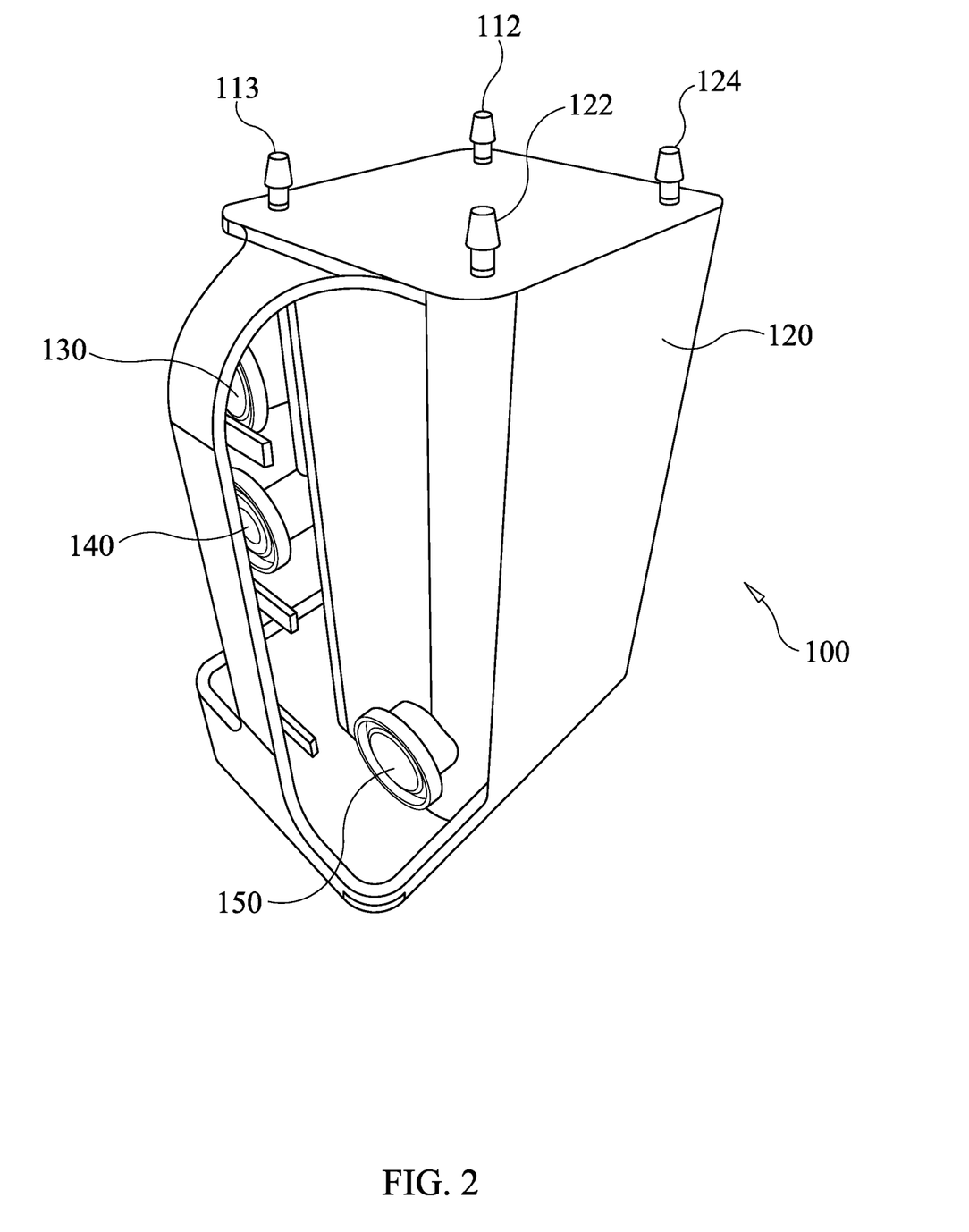
FIG. 2 is a line drawing evidencing an alternate view from the mixing vessel side of the flow kit of FIG. 1.

FIG. 2 shows a perspective view of the alternate, mixing vessel 120 side of the flow kit 100 of FIG. 1. Processed serum solution from the separate purification device (not pictured) is reintroduced to the kit via flexible tubing attached to the mixing vessel input line 122, and thus directly into the mixing vessel 120. Also embodied as a line to the external surface of the kit and connected to the mixing vessel is a vent 124, which can also be used as a filter attachment in certain embodiments. Another point of input is a mixing vessel solution input line 121, preferably located sub-surface to enable siphoning for diafiltration, which can be used to introduce further fluid for adjustment or processing of the serum product inside the mixing vessel, after which mixing the processed serum flows into a product output line 123, for delivery to another kit (not pictured) for further processing or to a collection vessel (not pictured). An auxiliary connection 150, embodied as a circular port, is also provided between the outside of the kit body and the mixing vessel, such auxiliary connection available for one or more uses, including but not limited to sample collection, pH probe connection, or insertion of a stir bar.

Figure 3:
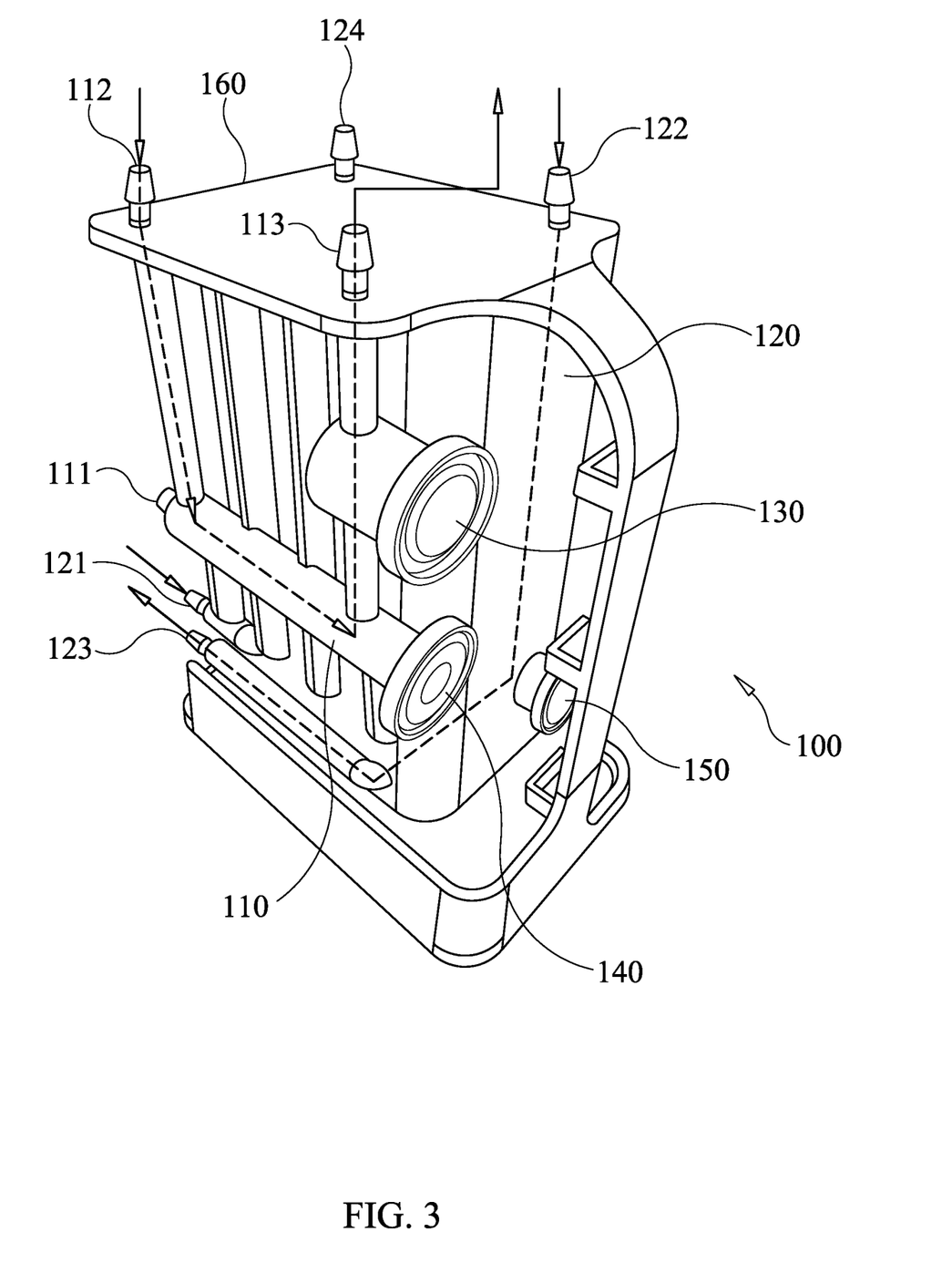
FIG. 3 is a line drawing evidencing a top view of the flow kit of FIG. 1.

FIG. 3 shows a top view emphasizing the various points of connection on top of the flow kit 100 for the fluids to be put into and extracted from the kit. On near side of the flow kit comprising the static mixer 110, the top of the flow kit comprises a product input line 112 for introduction of serum and a static mixer outlet line 113 for transmission of the serum after processing in the static mixer 110 to a filtration device or chromatography column (not pictured). On the side of the kit body facing rearward is a static mixer input line 111 for the introduction of solutions to treat and purify the serum such as pH adjusting agents, a mixing vessel input line 121 for the introduction of treatment and purification agents and a product outlet line 123, for the outflow of treated serum product either to a collection vessel or another flow kit (not pictured).

In the central and farther side of the top of the flow kit, containing the mixing vessel 120, the top of the flow kit comprises a mixing vessel input line 122 carrying processed serum from the filtration device or chromatography column (not pictured) into the mixing vessel for further processing, and a mixing vessel filter attachment 124 for the optional attachment of a vent filter or for venting purposes.

Each component evidenced on top of the flow kit is a port embodied as a barbed tube connection onto which a flexible tube or line may be overlaid. Each such component is manufactured through 3d printing, injection molding or a similar process as a part of the larger flow kit 100 and thus is integral to the invention. The flared port barb 160 of each component provides a stable, anchoring platform around which a flexible plastic or rubber tube may be arranged to create a seal to prevent leakage or contamination as fluids are introduced into or extracted from the flow kit.

Figure 4:
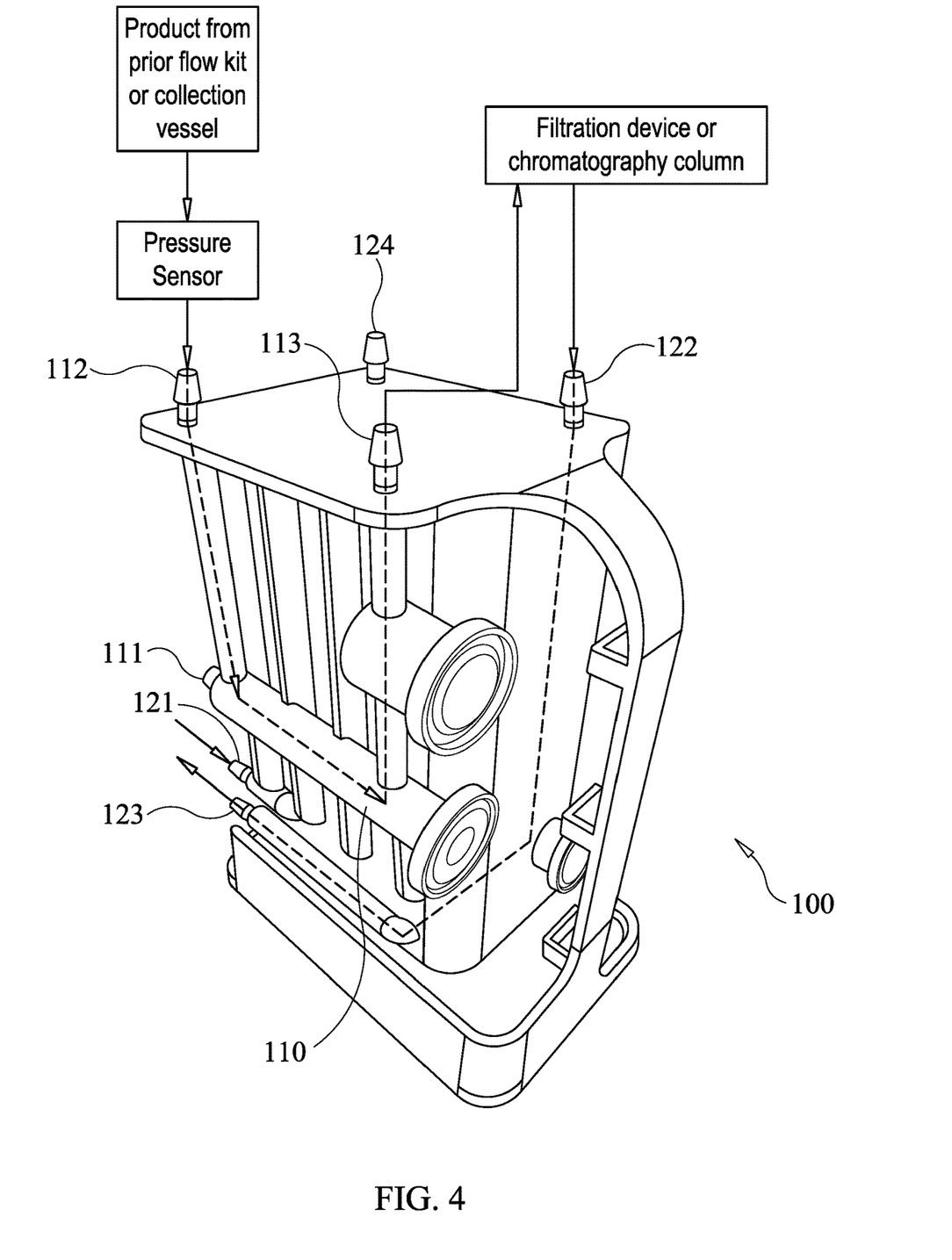
FIG. 4 is a line drawing evidencing a perspective view of the flow kit of FIG. 1 with arrows showing the fluid flow path.

FIG. 4 shows another perspective view of the flow kit 100 embodiment of FIG. 1, also including arrows indicating the flow pattern of fluids (not pictured) moving into and out of the flow kit. As pictured arrows indicate the following movement: the therapeutic protein serum product moves in through product input line 112, through static mixer 110 for processing and out through static mixer outlet line 113 to the filtration device or chromatography column, back in through mixing vessel input line 122, through the mixing vessel 120, and finally out through the product outlet line 123 and on to either a final collection vessel or to another flow kit for further processing. In addition to the flow paths of the therapeutic protein serum itself, the dotted arrows indicated pathways for input of adjusting or processing solutions into static mixer 110 through static mixer solution input line 111 and into mixing vessel 120 through mixing vessel solution input line 121.

Figure 5:
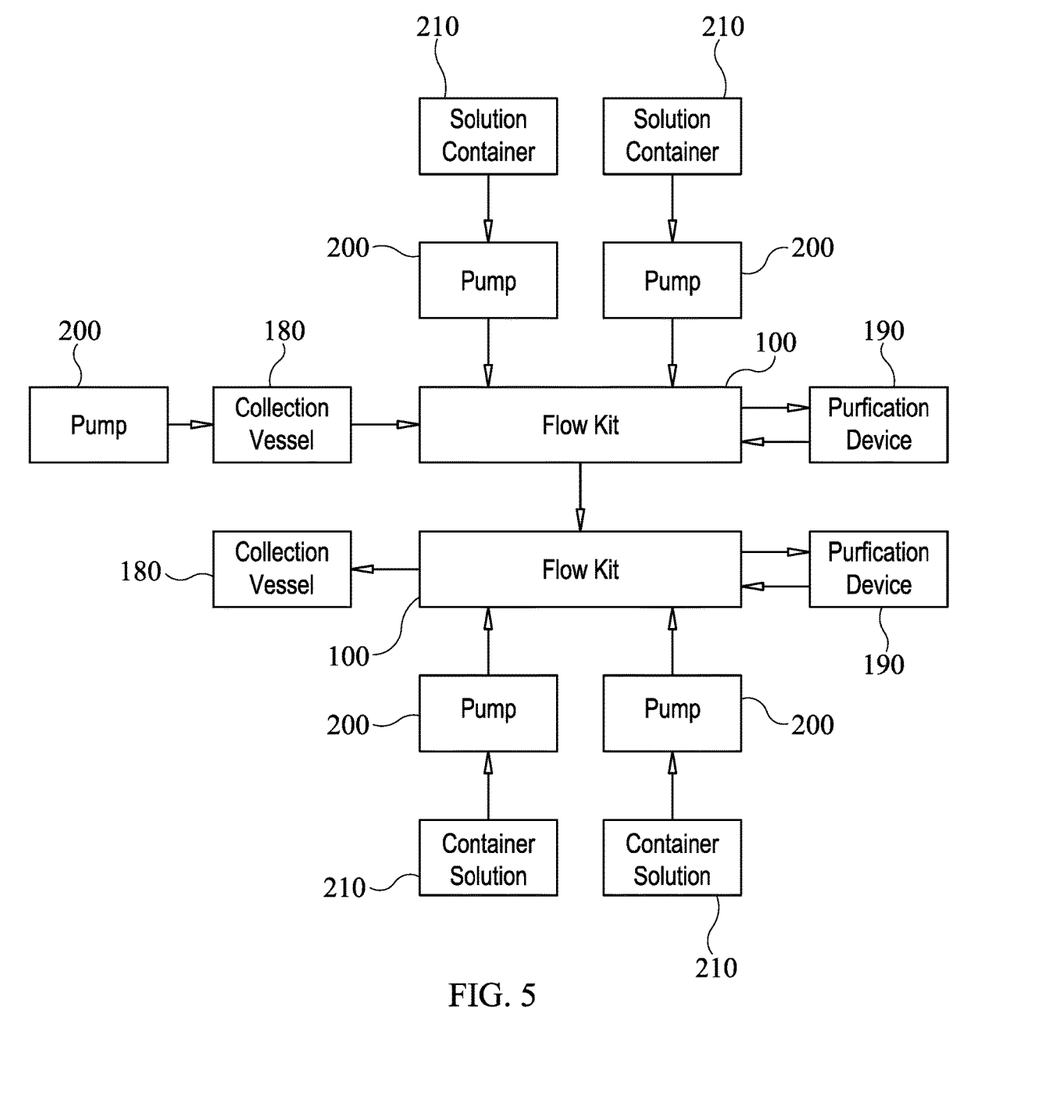
FIG. 5 is a flow chart evidencing a therapeutic protein serum purification system comprising multiple flow kits as shown in the preceding figures.

FIG. 5 shows a flow chart evidencing the flow patterns of serum through a system comprising the flow kits 100 and other devices pictured in FIG. 4. The fluid begins in a collection vessel 180, is pumped by a pump 200 to a first flow kit 100, thence to a purification device 190 comprising either a filter or chromatography column, back to the first flow kit, thence to a second flow kit 100, thence to a second purification device, back to the second flow kit, and then to a final collection vessel 180. As the fluid passes through each flow kit, adjusting solutions are added optionally via one or two pumps 200, each pumping solution from a solution container 210. Placement of pumps in the system may vary between different iterations, for example residing between the solution container or collection vessel and flow kit, or alternatively on the opposite side of the flow kit from such solution container or collection vessel. Additional steps comprising additional flow kits, purification devices, etc. may be added without limitation. Arrows in the chart evidence flexible tubing attaching the components. Additional components, such as pH probes or sampling devices, may optionally be attached to one or more flow kits and not pictured.

PARTS OF THE INVENTION

100 Flow Kit
110 Static mixer
111 Static mixer solution input line
112 Product input line
113 Static mixer outlet line
120 Mixing vessel
121 Mixing vessel solution input line
122 Mixing vessel input line 123 Product outlet line
124 Mixing vessel filter attachment
130 pH probe connection
140 Sampling connection
150 Auxiliary connection
160 Port barb
170 Flexible tubing
180 Collection vessel
190 Purification Device (i.e., filter or chromatography column)
200 Pump
210 Solution container

I claim:

1. A flow kit for the continuous purification of a therapeutic protein serum product, made of rigid plastic, forming a single, compact, integrated piece comprising a static mixer with a first side and a second side, wherein a plethora of input and outlet lines for the products and the addition of adjusting or processing solutions, a pH probe connection and a sampling connection are vertically oriented on the first side and a vented mixing vessel is located on the second side with input and outlet lines.

2. The flow kit of claim 1, wherein the manufacturing process is taken from the group consisting of 3D printing, injection molding, low-pressure molding such as gas-assist molding or structural-foam molding, coinjection, in-mold polymerization, blow molding, shaped thermoforming or another similar method.

3. The flow kit of claim 1, wherein the plastic is HP 3D High Reusability PA 12 or another commercially available plastic with similar characteristics.

4. The flow kit of claim 1, wherein the flow kit is made of carbon fiber.

5. The flow kit of claim 1, wherein the kit is connected by flexible tubing to a separate purification device such as a filter or chromatography column.

6. The flow kit of claim 1, wherein the kit is disposable.

7. The flow kit of claim 1, wherein the kit is detachable, cleanable and reusable.

8. The flow kit of claim 1, wherein the kit processes the therapeutic protein serum by optionally mixing with an adjustment solution(s) in the static mixer, delivering the serum to a separate purification device, then optionally mixing the serum with adjustment solution(s) in the mixing vessel.

9. A therapeutic protein serum continuous purification system comprising one or more powered pumps, multiple solution containers, and multiple flow kits of claim 1, such flow kits interspersed with multiple filters and/or chromatography columns and a collection vessel, wherein each component is connected by flexible tubing.

10. A method of purifying a therapeutic protein serum comprising the steps of:
    Connecting a supply of unpurified protein serum to a first flow kit of claim 1, and into a static mixer of the kit,
    Connecting a supply of a first adjustment solution(s) to the static mixer,
    Mixing the first adjustment solution(s) and serum in a static mixer,
    Directing the serum from the static mixer into a separate filter or chromatography column for processing,
    Directing the serum from the separate filter or chromatography column into the flow kit and into a mixing vessel,
    Connecting a supply of second adjustment solution(s) to the mixing vessel,
    Mixing the first adjustment solution(s) and serum in a mixing vessel, and
    Directing the serum from the mixing vessel out of the kit and to another separate flow kit or a collection vessel.

11. The flow kit of claim 1, wherein the flow kit dimensions are approximately 12.5 cm in length, 8 cm in width and 15.5 cm in height.

* * * * *